United States Patent [19]
Stephens et al.

[11] Patent Number: 5,709,671
[45] Date of Patent: Jan. 20, 1998

[54] TROCAR HAVING AN IMPROVED TIP CONFIGURATION

[75] Inventors: Randy R. Stephens, Fairfield; Steven G. Yapp, Loveland; Salvatore Privitera, West Chester; Richard F. Schwemberger; Darrel Powell, both of Cincinnati, all of Ohio

[73] Assignee: Ethicon Endo-Surgery, Inc., Cincinnati, Ohio

[21] Appl. No.: 543,455

[22] Filed: Oct. 16, 1995

[51] Int. Cl.⁶ .................................................. A61M 5/00
[52] U.S. Cl. ........................... 604/264; 604/164; 606/185
[58] Field of Search ........................... 604/264, 164–170; 606/167, 172, 185

[56] References Cited

U.S. PATENT DOCUMENTS 4,535,773  8/1985  Yoon ........................................ 604/51
5,314,417  5/1994  Stephens et al. ........................ 604/264
5,350,393  9/1994  Yoon ........................................ 606/185
5,522,831  6/1996  Sleister et al. .......................... 606/182

FOREIGN PATENT DOCUMENTS 0 647 434 A2  4/1995  European Pat. Off. .
WO 94/04082  3/1994  WIPO .

*Primary Examiner*—John D. Yasko
*Attorney, Agent, or Firm*—Matthew S. Goodwin

[57] ABSTRACT

A safety-shielded trocar having an obturator with a linear cutting edge surface defining a base width substantially less than the diameter of the safety shield is disclosed. When the trocar is inserted through tissue, the tissue dilates from the width of the linear incision to accommodate the size of the safety shield of the trocar, thus making it possible to provide an access opening greater than the incisional width made by the linear cutting edge surface of the obturator. In a preferred embodiment, the safety shield has a shield tip region which is asymmetric to facilitate the dilation of the tissue as the trocar is inserted.

13 Claims, 4 Drawing Sheets

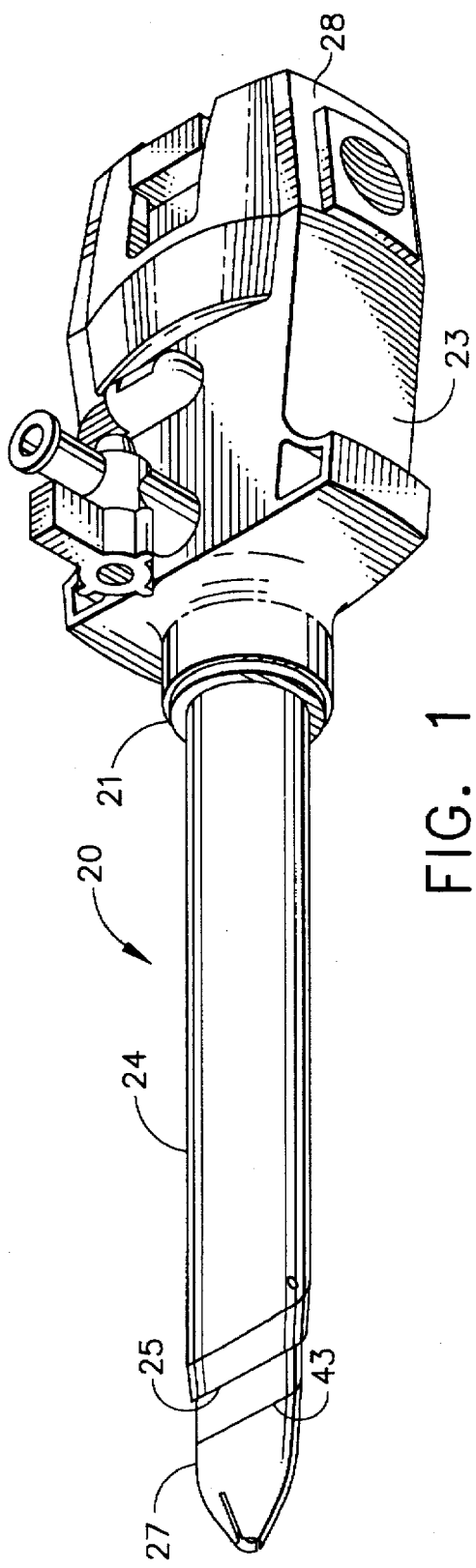
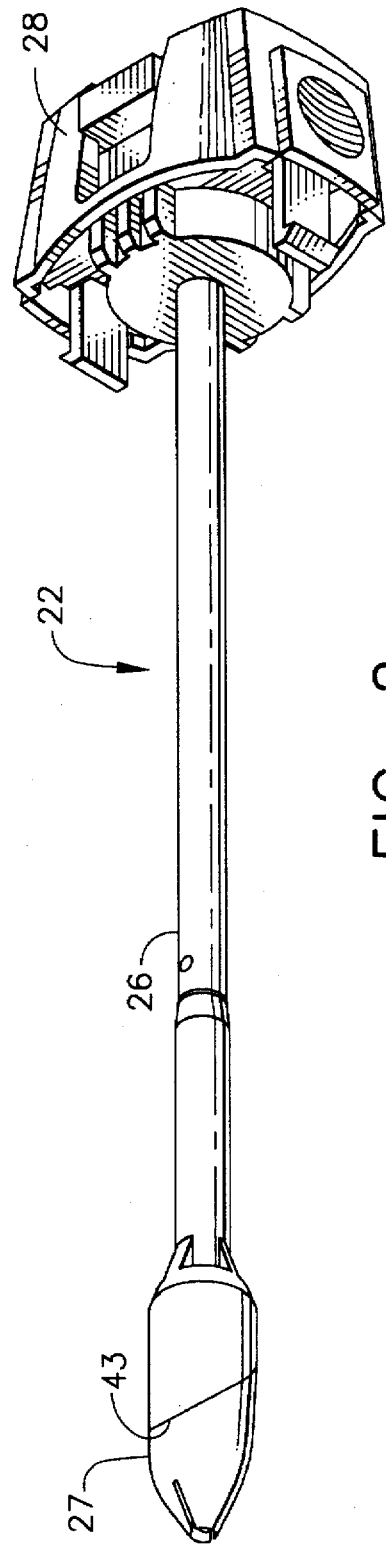
FIG. 1
FIG. 2

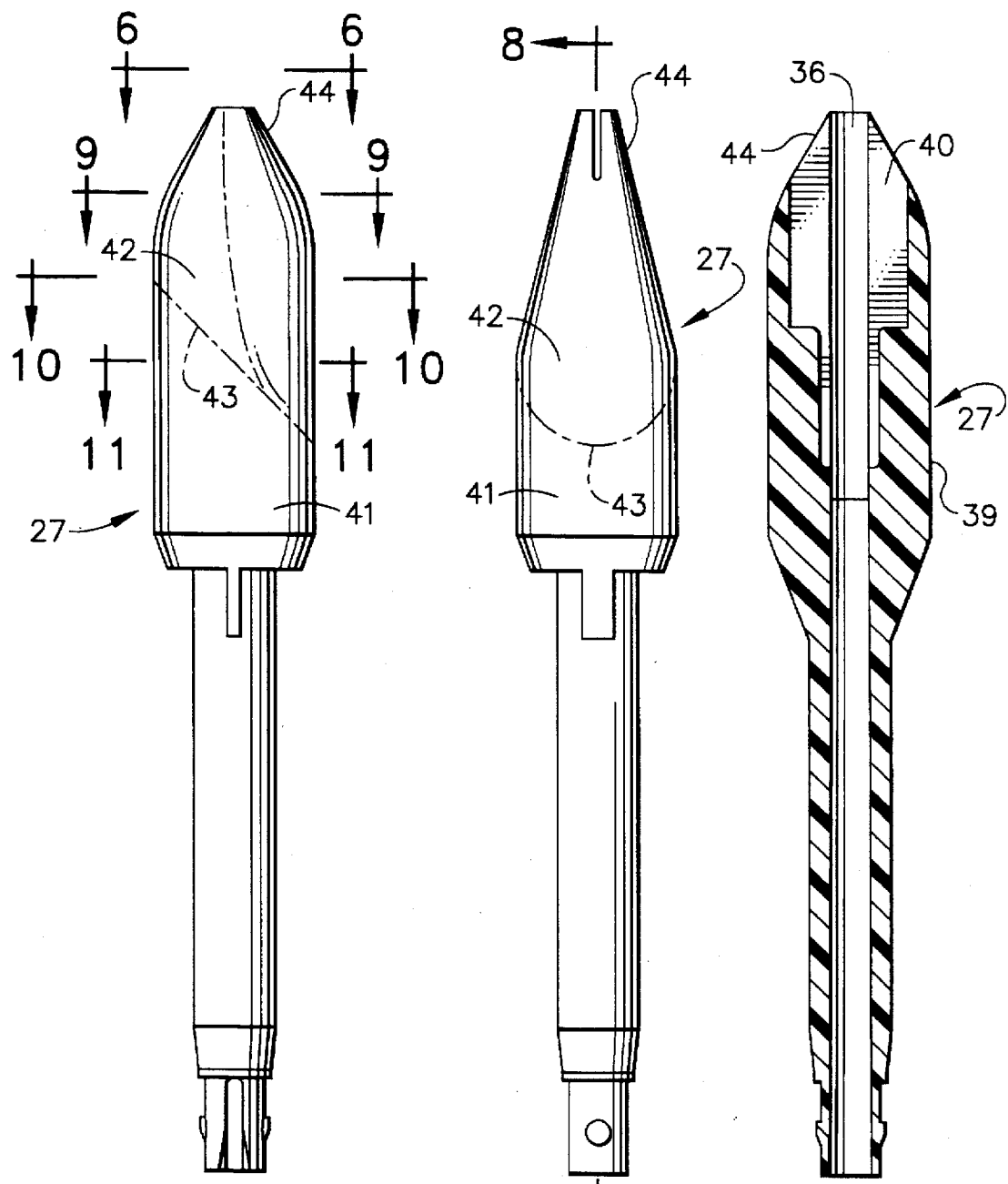
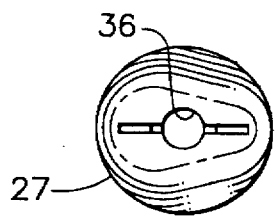
FIG. 5
FIG. 6
FIG. 7
FIG. 8

TROCAR HAVING AN IMPROVED TIP CONFIGURATION

BACKGROUND OF THE INVENTION

This invention relates to a trocar with an improved tip configuration. More specifically, it relates to a safety-shielded trocar which incorporates a particularly advantageous puncturing tip and shield geometrical configuration.

The surgical trocar has become the mainstay in the development and acceptance of endoscopic surgical procedures. Endoscopic surgery involves the performance of surgery through a number of openings having a relatively small diameter. These openings are made with the trocar, which typically includes a trocar obturator and a trocar cannula. The obturator is the piercing implement which punctures the body wall to make the opening. The obturator slidingly fits into the trocar cannula, which is essentially an access tube. The obturator is initially fitted into and through the cannula so that the piercing tip of the obturator extends from the distal end of the cannula. Pressure is exerted on the body wall with the piercing tip, and the puncture is made through the body wall. Once the puncture is made, the obturator is withdrawn from the cannula. The cannula then provides a small diameter passageway into and through the body wall to provide access for additional surgical instrumentation to the desired surgical site.

One of the significant advances in the development of the trocar is described in U.S. Pat. No. 4,535,773. This patent describes the use of a spring-loaded safety shield interposed between the obturator and inner wall of the trocar cannula. In its unbiased position, the shield covers the puncturing tip of the obturator. When pressure is applied against the body wall, the shield retracts to expose the blade. When the body wall is punctured, the pressure is relieved and the safety shield springs back to cover the puncturing tip. In this way, inadvertent puncture of internal organs is substantially lessened.

Them is a constant drive within the surgical community to use the smallest diameter trocar possible in performing endoscopic surgical procedures. The smaller the diameter, the less trauma the patient experiences because the wound site left behind is correspondingly smaller. The surgical patient experiences less pain and recovers more quickly. Further driving the effort to reduce the size of trocars is the widely held belief that wound sizes less than about 10 mm do not require suturing for wound healing. If suturing is unnecessary, surgeon time and expense is eliminated and patient trauma is reduced.

Conventional trocars typically have obturators with conical or pyramidal puncturing tips. Although these tip configurations have reduced the force necessary to penetrate the body wall, the tip punctures an amount of tissue corresponding to the outer diameter of the conical or pyramidal obturator tip. Therefore, when a 12 mm trocar is used, the 12 mm incision made by the trocar through the tissue must be sutured following completion of the surgery.

An obturator tip configuration which successfully minimizes trauma to the patient is described in U.S. Pat. No. 5,314,417. In contrast to conventional obturators with conical or pyramidal tips, the obturator tip of the trocar described in the '417 patent is a flat razor blade. The razor blade is triangular, and has a width equal to the inner wall of the trocar cannula. The blade makes a slit-like incision, and this incision is expanded radially as the tissue contacts the safety shield of the trocar. As the tissue is further penetrated, the incision expands to the outer diameter of the safety shield and the trocar cannula. Although this trocar represents substantial progress in the development of a trocar which provides an effectively smaller diameter opening in the body wall, it would be desirable if the effective diameter of the trocar could be further reduced.

Accordingly, it would be highly desirable to develop a trocar which can provide access for instruments having a larger diameter than the size of the puncturing tip of the obturator. More particularly, it would be desirable to develop an obturator tip for a trocar with a razor blade configuration which has a blade width less than the diameter of instruments which are subsequently inserted through the trocar. In other words, it would be desirable if the tip configuration of the trocar could take full advantage of the design of the obturator blade and safety shield to facilitate the expansion and dilation of the tissue as the trocar is inserted. If less tissue can be directly punctured with the trocar because more tissue is being dilated as the trocar is penetrating through the tissue, then the size of the wound which the trocar leaves behind following surgery can be substantially reduced. This would correspondingly reduce post-operative pain which the surgical patient would experience and shorten the recuperative period. Obviously, the development of such a trocar which will provide all of these benefits would represent a substantial leap forward toward the goal of making trocars as small as practically possible.

SUMMARY OF THE INVENTION

The invention is a trocar for piercing a body wall. The trocar comprises an obturator and a safety shield.

The obturator has a piercing tip with first and second planar surfaces generally parallel to each other. These surfaces converge to a curing edge surface at a first end of the surfaces. The planar surfaces define a base at an opposite end of the surfaces, and the base has a base width.

A safety shield encases the piercing tip of the obturator. The safety shield is retractable from an extended position to a retracted position. In the extended position, the safety shield encloses the cutting edge surface of the piercing tip of the obturator. In the retracted position, the cutting edge surface of the piercing tip of the obturator is exposed through the safety shield. In addition, the shield has a wall defining a shield diameter.

Importantly, the base width of the piercing tip of the obturator is substantially less than the diameter of the safety shield.

Significantly, when the body wall is pierced with the trocar, the tissue expands radially and dilates as the safety shield is inserted through the linear incision made by the cutting edge surface of the piercing tip of the obturator. The dilation and expansion of the tissue occurs because the base width of the planar surfaces of the piercing tip of the obturator is substantially less than the diameter of the safety shield. Therefore, as the safety shield is inserted through the incision, the tissue must expand and dilate to accommodate the difference between the geometrical configuration of the shield and the cutting surfaces of the piercing tip. In other words, when the shield comes into contact with the tissue, the tissue must expand linearly from the base width of the piercing tip of the obturator to the diameter of the safety shield. Correspondingly, the tissue must also dilate radially to transition from the linear incision to the non-linear configuration of the safety shield.

In a particularly preferred embodiment, the safety shield has a shield tip region which is asymmetric. It has a first tip width which is parallel to the planar surfaces of the piercing tip of the obturator. The first tip width is substantially greater than a second tip width perpendicular to the first tip width. The safety shield preferably includes a body region which intersects with the shield tip region at a beveled surface line. Further, the trocar includes a cannula sleeve from which the safety shield protrudes, and the sleeve has a beveled tip which is generally parallel to the beveled surface line on the shield. In this preferred embodiment of the invention, the safety shield configuration enhances the ability of the trocar to smoothly dilate and expand the tissue from the linear incision made by the cutting edge surface of the piercing tip of the obturator.

Surprisingly, the base width of the piercing tip, and therefore the length of the actual incision made in the body wall, can be substantially less than the size of the cannula associated with the trocar. Since the tissue dilates during insertion, the actual size of the incision is less than the outside diameter of the cannula sleeve. More specifically, by way of example without limitation, the trocar of this invention can be a 12 mm trocar with a corresponding 12 mm cannula sleeve through which 12 mm instruments can be inserted and withdrawn, and yet the actual size of the linear incision made by the cutting edge surface of the piercing tip of the obturator can be substantially less than 10 mm. Consequently, when the trocar is removed following surgery, the size of the incisional wound left behind is substantially less than the outside diameter of the cannula sleeve. Therefore, it becomes unnecessary for the surgeon to suture the incisional wound site, and the patient correspondingly suffers far less trauma and recuperates in a more timely fashion.

The trocar of this invention can be used for any applications where trocars previously have been used or contemplated. Of course, it is particularly adapted for those applications where it is desired to minimize the size of the openings made in the body wall during endoscopic surgery.

BRIEF DESCRIPTION OF THE DRAWINGS

FIG. 1 is a perspective view of a preferred trocar of this invention.

FIG. 2 is a perspective view of the obturator assembly for use with the trocar of FIG. 1.

FIG. 5 is a side elevational view illustrating the preferred configuration of the safety shield of the obturator assembly.

FIG. 6 is a front end elevational view taken along line 6—6 of FIG. 5.

FIG. 7 is a bottom view illustrating the preferred configuration of the safety shield of the obturator assembly.

FIG. 8 is a cross sectional view illustrating the safety shield of the obturator assembly taken along line 8—8 of FIG. 7.

DETAILED DESCRIPTION OF THE PREFERRED EMBODIMENT

Figure 3:
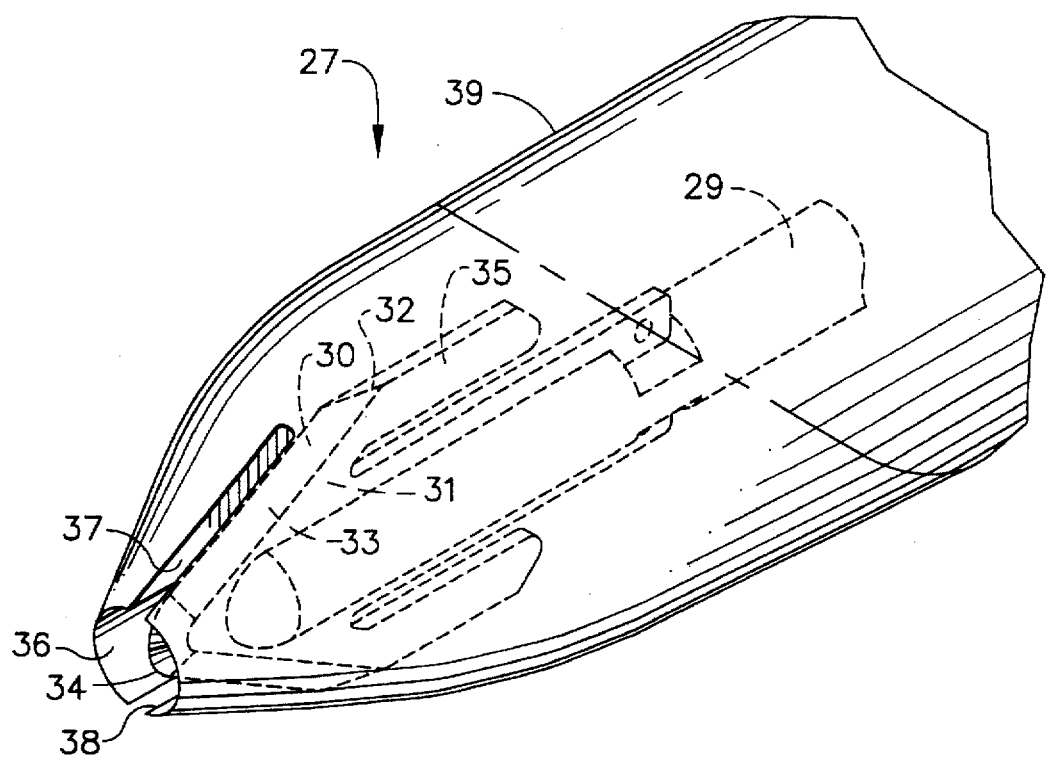
FIGS. 3 and 4 are perspective views of the distal end of the obturator assembly with the safety shield in its extended and retracted positions, respectively.

The preferred trocar 20 of this invention is illustrated generally in FIGS. 1 and 2. The trocar has a cannula 21 and an obturator assembly 22. The cannula has a housing 23 and an elongated, cylindrical sleeve 24 extending from the housing. The distal end of the sleeve has a beveled surface 25. The obturator assembly has a long cylindrical sleeve 26. At the distal end of the sleeve, there is a safety shield 27 covering the piercing tip of the obturator (the piercing tip is not shown in FIG. 2). The obturator sleeve is attached at its proximal end to an obturator housing 28. The obturator assembly is inserted through the cannula. The diameter of the safety shield generally corresponds with the inner wall diameter of the trocar cannula, so that the obturator assembly slides through the cannula sleeve. The distal end of the obturator assembly, including the safety shield, protrude from the beveled distal end of the cannula sleeve when the obturator assembly is fully inserted through the cannula. When the obturator assembly is fully inserted, the obturator housing is secured to the proximal end of the cannula housing. After the body wall is penetrated, the obturator assembly is withdrawn from the cannula, and the cannula is used as an access portal for the passage of various endoscopic instruments.

Figure 4:
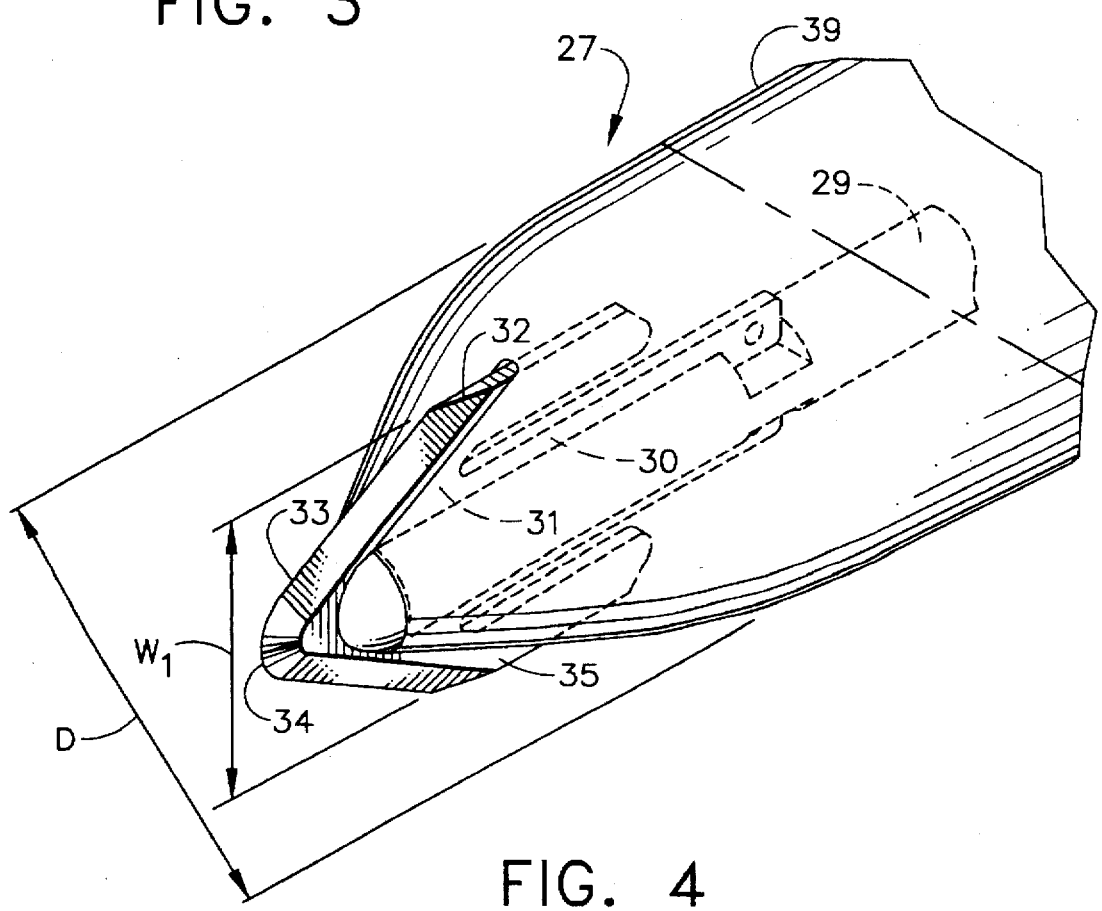

Referring now to FIGS. 3 and 4, an obturator 29 having a piercing tip 30 is encased within the safety shield 27 at the distal end of the obturator assembly. The piercing tip of the obturator is attached to the distal end of the obturator. The attachment of the piercing tip to the stem of the obturator is described in detail in commonly assigned, copending application Ser. No. 08/543,547, filed Oct. 16, 1995. The piercing tip has first and second planar surfaces, 31 and 32, respectively, generally parallel to each other. At the forward-most end of the penetrating tip, the surfaces converge to a cutting edge surface 33. The cutting edge surface is triangular, and has a rounded apex 34. Adjacent the rearwardmost portion of the cutting edge surface, the piercing tip has a base 35 defining a base width, $W_1$, as shown in FIG. 4.

The safety shield of the obturator assembly is movable from an extended position illustrated in FIG. 3 to a retracted position illustrated in FIG. 4. When the shield is in its extended position, the shield covers the cutting edge surface of the piercing tip of the obturator to prevent inadvertent puncture. When pressure is applied against the shield during piercing of the body wall, the shield moves to its retracted position. When the shield is in its retracted position, the triangular cutting edge surface of the piercing tip of the obturator is exposed through the shield. The distal end of the shield has a central aperture 36 and first and second slots, 37 and 38, respectively, through which the cutting edge surface of the penetrating tip is passed.

The safety shield of the obturator assembly has a wall 39 which defines shield diameter. The shield diameter is designated as D in FIG. 4. As illustrated in FIG. 4, diameter, D, of the safety shield taken in a plane parallel to the planar surfaces of the piercing tip is substantially greater than the base width, $W_1$, of the piercing tip. Illustrating this particular feature of the invention further, FIG. 8 shows that the safety shield contains a blade slot 40 for receiving the piercing tip of the obturator within the safety shield. As depicted in FIG. 8, the size of the blade slot is substantially less than the diameter of the safety shield.

Referring now to the remaining figures, the unique configuration of the safety shield 27 to promote smooth expansion and dilation of tissue is illustrated. The shield has a body region 41 and a shield tip region 42 extending from the body region. The body region has a circular cross-section, and the shield tip region has an asymmetrical, non-circular cross-section (see FIGS. 6 and 9–11). The body and shield tip regions of the safety shield intersect at a beveled surface line 43. When the obturator assembly is inserted through the trocar cannula, the beveled surface line 43 on the safety shield is parallel to the beveled distal end 25 of the cannula sleeve 24 (see FIG. 1).

Figure 9:
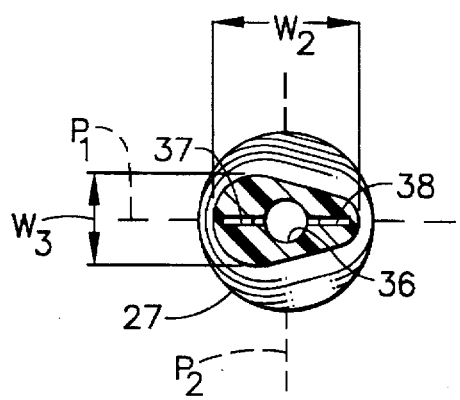
FIG. 9 is a front end elevational view taken along line 9—9 of FIG. 5.
Figure 10:
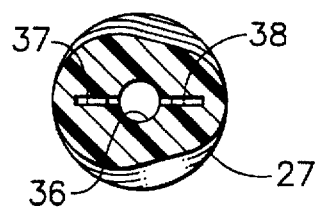
FIG. 10 is a front end elevational view taken along line 10—10 of FIG. 5.
Figure 11:
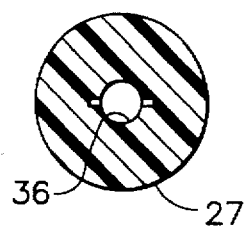
FIG. 11 is a front end elevational view taken along line 11 of FIG. 5.
Figure 12:
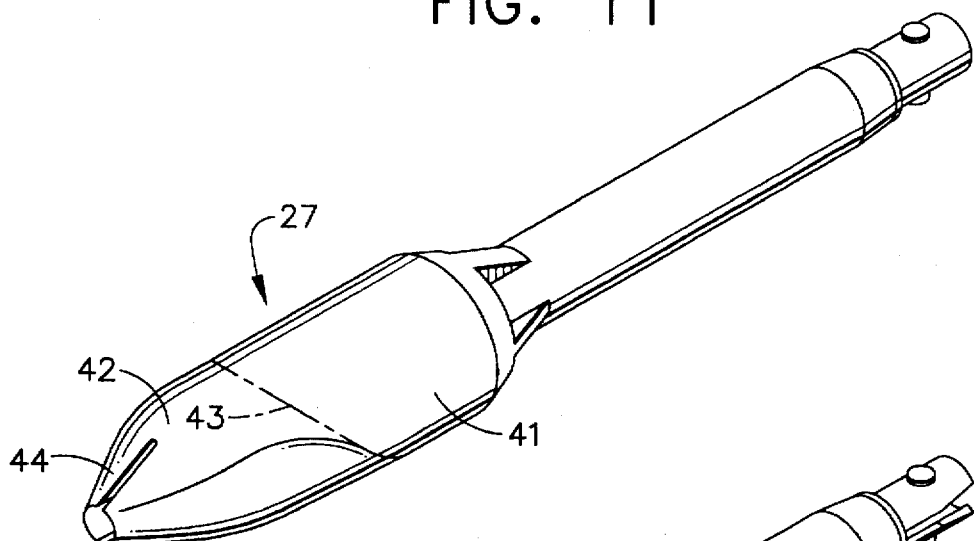
FIG. 12 is a perspective view illustrating the preferred configuration of the safety shield of the obturator assembly.
Figure 13:
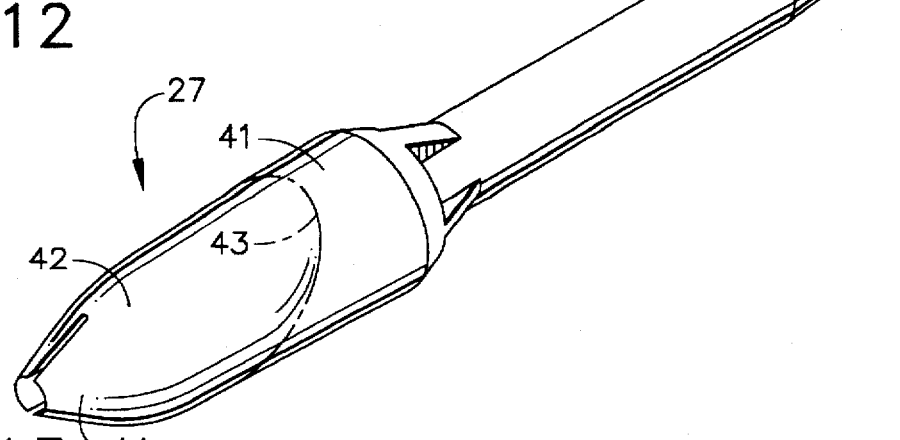
FIG. 13 is a perspective view illustrating the preferred configuration of the safety shield of the obturator assembly in which the safety shield is rotated 180° about the center line with respect to FIG. 12.

The safety shield can best be described as pear-shaped at that portion of the shield tip region adjacent the distal end 44 of the safety shield (see FIG. 9). The first and second slots at the distal end of the shield tip region for receiving the cutting edge surface of the piercing tip of the obturator define a first plane, designated as $P_1$ in FIG. 9, parallel to the slots and intersecting the safety shield. The slots also define a second plane, designated as $P_2$ in FIG. 9, which is perpendicular to the slots. Plane $P_1$ further defines a width, designated as $W_2$ in FIG. 9, parallel to plane $P_1$. Correspondingly, plane $P_2$ also defines a width, designated as $W_3$, parallel to plane $P_2$. A unique feature of the preferred embodiment is that the width $W_2$ is substantially greater than the width $W_3$ adjacent the distal end 44 of the shield tip region. At positions rearward of the distal end, the difference between widths $W_2$ and $W_3$ becomes less pronounced (see FIG. 10). Widths $W_2$ and $W_3$ become substantially the same adjacent the beveled surface line 43, so that the cross-section of the body region of the safety shield is essentially round (see FIG. 11).

Although this invention has been described in connection with the most preferred embodiment, numerous additional embodiments are contemplated and fall well within the scope and spirit of the claimed invention. This detailed description of the invention is intended only to provide the reader with a detailed explanation of the most preferred embodiment of the invention, so that the invention will be fully understood to those skilled in this art.

What is claimed is:

1. A trocar for piercing a body wall, said trocar comprising:

a) an obturator having a piercing tip with first and second planar surfaces generally parallel to each other, said surfaces converging to a cutting edge surface at a first end of said surfaces, and said surfaces defining a base at an opposite end of said surfaces, said base having a base width; and b) a safety shield encasing said piercing tip, said safety shield retractable from an extended position wherein said shield encloses said cutting edge surface of said piercing tip to a retracted position wherein said cutting edge is exposed through said shield, said shield having a wall defining a shield diameter;

wherein said base width is substantially less than said shield wall diameter.

2. The trocar of claim 1 wherein said cutting edge surface is a generally triangular surface having an apex.

3. The trocar of claim 2 wherein said shield has a body region and a shield tip region extending from said body region, said body and shield tip regions intersecting at a beveled surface line.

4. The trocar of claim 3 further comprising a cannula sleeve from which said safety shield protrudes, said sleeve having a beveled tip.

5. The trocar of claim 4 wherein said beveled surface line of said safety shield is generally parallel to said beveled tip of said cannula sleeve.

6. The trocar of claim 5 wherein said body region has a circular cross-section.

7. The trocar of claim 6 wherein said shield tip region has a non-circular cross-section.

8. The trocar of claim 7 wherein said shield tip region has a distal end, and said distal end of said shield tip region has a central aperture and first and second slots thereon for receiving said cutting edge surface of said piercing tip through said safety shield.

9. The trocar of claim 8 wherein said first and second slots define a first plane parallel to said slots and intersecting said safety shield.

10. The trocar of claim 9 wherein said first and second slots define a second plane perpendicular to said slots and intersecting said safety shield.

11. The trocar of claim 10 wherein said shield tip region defines a first tip width parallel to said first plane, and a second tip width parallel to said second plane.

12. The trocar of claim 11 wherein said first tip width is substantially greater than said second tip width adjacent said distal end of said shield tip region.

13. The trocar of claim 12 wherein said cross-section of said shield tip region adjacent said distal end of said shield tip region is pear-shaped.

* * * * *